United States Patent [19]
Bresson-Rival et al.

[11] Patent Number: 5,904,921
[45] Date of Patent: May 18, 1999

[54] STABILIZED COMPOSITIONS OF SUPEROXIDE DISMUTASE OBTAINED FROM GERMINATED PLANT SEEDS

[75] Inventors: Delphine Bresson-Rival, Lyon; Patrick Boivin, Nesseirr; Guy Linden, Heillecourt; Eric Perrier, Les Cotes d'Arey; Gérard Humbert, Jarville la Malgrange, all of France

[73] Assignee: Coletica, Lyon, France

[21] Appl. No.: 08/787,104

[22] Filed: Jan. 22, 1997

[30] Foreign Application Priority Data

Apr. 3, 1996 [FR] France .................................. 96 04165

[51] Int. Cl.$^6$ .......................... A61K 38/54; A61K 38/43; A61K 38/44; C12N 9/96; C12N 9/02
[52] U.S. Cl. ....................... 424/94.3; 424/94.1; 424/94.4; 435/188; 435/189
[58] Field of Search ................................. 424/94.1, 94.3, 424/94.4; 435/188, 189

[56] References Cited

U.S. PATENT DOCUMENTS

| | | | |
|---|---|---|---|
| 3,637,640 | 1/1972 | Huber ....................................... | 530/401 |
| 3,773,929 | 11/1973 | Huber et al. ............................... | 514/21 |
| 3,997,402 | 12/1976 | Michelson ................................ | 435/189 |
| 5,179,012 | 1/1993 | Gudin et al. .............................. | 435/125 |
| 5,219,825 | 6/1993 | Gressel et al. ............................ | 504/117 |
| 5,362,494 | 11/1994 | Zysman et al. .......................... | 424/401 |
| 5,536,654 | 7/1996 | Gudin et al. .............................. | 435/189 |

FOREIGN PATENT DOCUMENTS

| | | |
|---|---|---|
| 2693208 | 1/1994 | France . |
| 92/19224 | 11/1992 | WIPO . |

OTHER PUBLICATIONS

J.Exp.Botany, vol. 44, No. 258, Jan. 1993 "Activities of Hydrogen Peroxide–Scavenging Enzymes in Germinating Wheat Seeds", Cakmak et al pp. 127–132.

Plant Physiol., vol. 59, No. 2, 1977 Superoxide Dismutases: Giannopolitis et al, pp. 315–318.

Physiol. Plantarum, Vo. 92, No. 3, "Four Cytosolic–type CuZn . . . " Steller et al, pp. 443–450.

Biochim. Biophys. Acta., vol. 317, No. 1, Jul. 12, 1993, "Isoenzymes of Superoxide . . . Germ", Beauchamp et al, pp. 50–64.

Biochim. Biophys. Acta., Vo. 1074, No. 2, Jul. 8, 1991, "Superoxide Anion and . . . Germination", Puntarulo et al, pp. 277–283.

Eur. J. Biochem, vol. 224, No. 1, Aug. 15, 1994, "Accumulation of Reactive . . . Seeds", Gidrol et al, pp. 21–28.

J. Am. Soc. Brewing Chem., vol. 51, No. 3, 1993, "Oxygen and Oxygen Radicals . . . Review", Bamforth et al, pp. 79–83.

Malting and Brewing Science, Chapman and Hall Ltd., Hough et al, pp. 95–105.

Database Cab Abstracts, 940708524, 1994, "The Effects of Gibberellic . . . Stages", Zeng et al, pp. 347–351.

Indian J. Exp. Biol., vol. 17, No. 7, 1979, "Effects of Glucose & 1,4–dinitrophenol . . . Bean", Ahuja et al, pp. 712–713.

*Primary Examiner*—Jon P. Weber
*Attorney, Agent, or Firm*—Dennison, Meserole, Pollack & Scheiner

[57] ABSTRACT

Germinated plant seeds are disclosed as a source of superoxide dismutase (SOD). The SOD is stabilized to temperatures of at least 45° C. when combined in a stabilizing composition comprising a peroxidase, a peroxidase cofactor, and a hydrophilic substance selected from sugars and polyols of less than 2,000 g/mole in molecular mass. The stabilized SOD compositions can be used in cosmetic, pharmaceutical or food compositions. Methods of treating mammals against the harmful effects of free radicals and against inflammation are also disclosed.

87 Claims, No Drawings

STABILIZED COMPOSITIONS OF SUPEROXIDE DISMUTASE OBTAINED FROM GERMINATED PLANT SEEDS

The present invention relates to an extraction/purification method of a superoxide dismutase from germinated plant seeds, and of its combination with a peroxidase accompanied by its enzymatic cofactor. This enzymatic complex stable in a cosmetic formulation is usable in cosmetic, pharmaceutical or food compositions. The present invention also relates to a method of treatment in the mammal against the harmful effects of free radicals especially inflammation, comprising administering to said mammal an amount of SOD extracted from germinated plant seeds which is effective against the harmful effects of free radicals.

INTRODUCTION

More precisely, the invention aims to obtain a superoxide dismutase (hereinafter referred to as the abbreviation SOD) from germinated plant seeds, i.e. having undergone a germination step, which possesses a high enzymatic activity, as well as a greater stability when this prepared SOD, after germination of plant seeds, is used in anti-radical compositions, in combination with another enzyme capable of destroying the by-products of the superoxide dismutation reaction, principally hydrogen peroxide ($H_2O_2$), such as catalases or peroxidases. The invention thus finds an advantageous application in cosmetic compositions, pharmaceutical or dermatological compositions, or in food compositions.

It is known that free radicals are atoms or molecules which possess an unpaired electron in their outside orbital. They are extremely unstable compounds which can react with the most stable molecules to pair up their electron.

The oxygen free radicals are continuously formed in the organism, in the mitochondria or during phagocytosis processes. The physical factors such as the exposure to ultra-violet radiation as well as the environment in which man evolves are also factors of high production of free radicals at the level of biological compounds. These factors are, for example, automobile pollution, tobacco, ionising radiations, etc.

The oxygen free radicals are formed by partial reduction of molecular oxygen. The capture of an electron by oxygen will generate the superoxide radical $O_2^{.-}$. This anion is not very reactive but it can generate very reactive radical species. The enzymatic dismutation of the superoxide anion by a SOD leads to the formation of hydrogen peroxide which, in the presence of ferrous iron, undergoes the Fenton reaction to form the very reactive hydroxyl radical $OH^.$.

In view of their high reactivity, the free radicals are capable of attacking any cellular constituent and are capable of provoking serious alterations: in the skin, the free radicals, the superoxide anion in particular, have collagen as major target but also attack elastin fibres, glycosaminoglycans and proteoglycans, intracellular DNA, cell membrane phospholipids, etc.

Collagen and elastin fibres directly capture the free radicals formed, resulting in various degradations: rupture of peptide chains and liberation of small peptides degraded by non-specific proteases, interchain bonds reducing elasticity.

Also, with the goal of counteracting the destructive effects of active forms of oxygen, it has become more and more necessary to prepare anti-oxidant-based compositions in every domain, and in particular in cosmetics, pharmacy and in food. In cosmetics, such compositions have been put on the market and are known as anti-age or anti-aging products.

PRIOR ART

The antioxidants currently used in cosmetics or in pharmacy are either chemical molecules which capture free radicals, or enzymatic systems whose major disadvantage is a very poor stability even at ambient temperature.

The lipophilic captors used are generally vitamin E and β-carotene, which are components of cell membranes which protect them from lipid peroxidation by reducing the peroxide radicals formed.

The hydrophilic antioxidants used are generally constituted by vitamin C, which acts in aqueous media with superoxide and hydroxyl radicals, but are also constituted by enzyme cofactors such as glutathion and zinc. Glutathion is the cofactor of many enzymes implicated in anti-radical defence (such as glutathion peroxidase, glutathion transferase, etc.) while zinc is the cofactor of copper-zinc SOD.

The enzyme used in cosmetics or pharmacy is SOD, whose role is to assure the almost instantaneous destruction of superoxide radicals which are potentially harmful to the organism and skin tissues. The reaction catalysed by SOD is the dismutation of the superoxide anion to give hydrogen peroxide according to the following chemical reaction:

$$O_2^{.-} + O_2^{.-} + 2H^+ \rightarrow H_2O_2 + O_2$$

Various enzymes exist (also known as isozymes of superoxide dismutase) which have been mainly isolated from wheat germ and the person skilled in the art may refer to the article of Beauchamp published in Biochimica et Biophysica Acta, 1973, 317, 50–64. In this article, Beauchamp reports to have isolated three SOD enzymes, one known as Mn SOD, which is sensitive to manganese and not inhibited by 0.2 mM cyanide, but is inactivated by the treatment of Tsuchihashi based on chloroform plus ethanol, as well as two other SODs of Cu—Zn SOD type which are inhibited by cyanide but not affected by the treatment with chloroform plus ethanol. The latter enzymes contain one $Cu^{2+}$ ion and one $Zn^{2+}$ ion per protomer and have a molecular weight in the order of 30,000 Daltons.

It is to be remembered that Cu—Zn SOD, present in cutaneous tissues, constitutes the first line of enzymatic defence against free radicals generated by ultra-violet rays. It is however interesting to note that the enzyme sees its detoxification very much reduced after irradiation of ultra-violet. This noting has driven cosmetology or pharmacy professionals to incorporate SOD in formulations in order to reduce the level of free radicals present in cutaneous tissues.

It has thus been proposed by L'Oréal in the U.S. Pat. No. 4,129,644 document to use the superoxide dismutase enzyme in a cosmetic composition and in a method comprising applications for maintaining the keratinic structure of the hair or for protecting the skin and the hair by the application of such a SOD. SOD was principally obtained from bovine blood or from different bacterial strains (claims 2 to 5).

L'Oréal has further proposed in the WO 92/19224 document a topical anti-free radical composition based on SOD from various origins (animal, human, bacterial, yeast or biotechnological) and a phosphonic acid as a metal-complexing agent for combatting skin aging and the protection of the skin against irradiations, basing themselves on the evidence that certain agents complexing inactivators of metals could, in certain cases, diminish the production of toxic hydroxyl radicals ($OH^-$).

It is further known from the FR-A-2 634 125 Nippon document a stabilized superoxide dismutase composition comprising SOD, a phosphate, an alkali metal chloride and sucrose (see claims). SOD is in fact extracted from human blood.

It is further known from the FR-A-2 693 208 Inocosm document, a method for obtaining an enzymatic composition of SOD of plant origin from cereals such as wheat germ by extraction with a liquid alcohol, removal of the polyphenols with the aid of a fixing agent such as polyamide or polyvinylpyrrolidone, washing and finally extraction of the proteins and enzymes again with liquid alcohol. The SOD activity obtained is very low and the use of solvents renders the SOD extract difficult to use.

Up to now, industrial SOD has been obtained by extraction from bovine erythrocytes available in large quantities from abattoirs.

On the other hand, although it is known at least from Beauchamp's article in Biochimica and Biophysica Acta, 1973, 317, pages 50–64, to extract SOD from wheat germ, and that at least one similar patent has been filed by Inocosm in 1992 (FR-A-2 693 208), the proportion of extraction of SOD of plant origin has been revealed to be very little due on the one hand to a low proportion of SOD in cereal germs and, on the other hand, by the use of a method of extraction in a solvent medium of poor yield.

Thus, the present invention has as principal aim to solve the novel technical problem consisting in furnishing a solution which allows obtaining SOD of plant origin in large quantities with a very good yield in a way to be used on an industrial scale, in particular in the cosmetic, pharmaceutical or food domain.

The present invention has also for aim to solve the novel technical problem consisting in providing a solution which allows obtaining an extremely active and also extremely stable SOD of plant origin, preferably in being capable of retaining 80% of its activity for 1 month (35 days) at ambient temperature and an activity in the order of 50% at 45° C. in allowing thus an effective incorporation in antiradical compositions, particularly in cosmetic, pharmaceutical or food preparations.

All these technical problems have been solved for the first time in a simple, safe and reliable way by the present invention, which constitutes an unexpected technical result which is not obvious to the person skilled in the art.

Thus, in a first aspect, the present invention relates to the use of germinated plant seeds as a source of extraction of SOD. In the framework of the invention, the meaning of the terms seeds and grains is equivalent.

In a particular embodiment, the plant seeds are cereal grains, leguminous plant seeds or oleaginous plant seeds. As cereals, any cereal can be used, in particular rye, maize, wheat or barley, preferably barley, amongst the usable barley varieties, spring or winter varieties can be used. For the leguminous plants, any leguminous plant seeds can be used but preferably lentils or peas. For the oleaginous plant seeds, any oleaginous plant seeds can be used, but preferably soya seeds.

In another implementation variant, the prior germination step comprises a germination for a period of time sufficient for increasing the SOD activity. This period of germination time is variable according to the cereals and the leguminous plants but is easy to determine by the person skilled in the art once he knows from the invention that the germination allows increasing the SOD activity.

In a currently preferred embodiment, the seeds are germinated for several days in a suspension in water, of preference in the presence of an agent which favors the germination at ambient temperature. Such an agent which favors the germination is of preference a compound belonging to the gibberellin family.

In a more preferred embodiment, the germination of the seeds is preceded by soaking in an aqueous solution at ambient temperature or in the cold for one or more days, for example two days. The starting up of the germination step is preferably carried out by the addition of an agent which favors the germination, preferably a compound belonging to the gibberellin family.

Other characteristics of the use according to the invention will appear as clearly from the claims and the description taken together.

In a second aspect, the present invention also relates to a SOD extraction method, characterized in that plant seeds having undergone a germination step are used as SOD source.

In an advantageous embodiment, the germination step comprises placing the plant seeds in suspension in an aqueous solution for several days at ambient temperature.

In a preferred embodiment, this germination step takes place in the presence of an agent which favors germination, again preferably constituted by a compound belonging to the gibberellin family.

In an advantageous implementation variant of the method, the germination step is preceded by a soaking step in an aqueous solution at ambient temperature or in the cold for one or more days, for example two days.

In yet another implementation variant of the method of the invention, the step of extraction of SOD from germinated seeds comprises grinding the germinated seeds followed by an extraction in a buffered aqueous solution having a pH near to 8 at ambient temperature for a period of time sufficient for effecting the SOD extraction, in general a few tens of minutes to one or several hours, followed by a filtration and recovery of the filtrate containing the SOD.

In an advantageous embodiment of the method of extraction, a more complete purification of SOD is carried out by treating the filtrate with a precipitation agent which allows eliminating the undesirable proteins including proteases and even lipoxygenase, and recovery of the non-precipitated fraction i.e. that constituting the supernatant which contains SOD.

In another even more advantageous implementation variant, a dialysis of the non-precipitated fraction containing SOD can be effected by dialysis against water or an aqueous solution, with a membrane having preferably a cut-off threshold comprised between 6,000 and 8,000 Daltons.

In yet another particularly preferred variant, a supplementary purification of the dialysed solution can also be carried out by proceeding with a purification on a chromatographic column which will preferably be constituted in the invention by a Sephadex QAE column with the aid of an appropriate elution solution.

In another advantageous embodiment of the method of the invention, a stabilization of the SOD obtained can be effected directly after the above-mentioned extraction step, i.e. before a more complete purification, or after purification, by the addition of an $H_2O_2$ trapping agent, such as a peroxidase preferably with a peroxidase cofactor (also known as peroxidase specific reducing substrate). Preferably, the amount of peroxidase added to the SOD expressed as a ratio of units of peroxidase to the units of SOD is in the invention about 10/400 while for the enzymatic cofactor of the peroxidase, this is preferably present in a concentration comprised between 0.001M and 1M with respect to the SOD/peroxidase complex.

In another advantageous embodiment of the method of the invention, a stabilization of SOD can also be effected by the addition after the extraction step, or after the purification step, of at least a sugar, in particular a monosaccharide or a disaccharide and/or at least a polyol, in particular a polyol having an average molecular weight comprised between 50 and 1000 g/mole. Preferably, the sugar or the polyol is added at a concentration comprised between 10 and 50% by weight of the SOD or of the final SOD complex, in the from of purified or crude extract.

After extraction with or without purification, an extract containing SOD is obtained which is determined by the method well known to the person skilled in the art, that of Nebot C., et al., published in Analytical Biochemistry, 1993, 214, pages 442–451.

Nebot's method is based on the property that any catalyst with a SOD activity can accelerate, at alkaline pH, the auto-oxidation of a reactant R1 to a chromophore absorbing in the visible light, according to the following reaction:

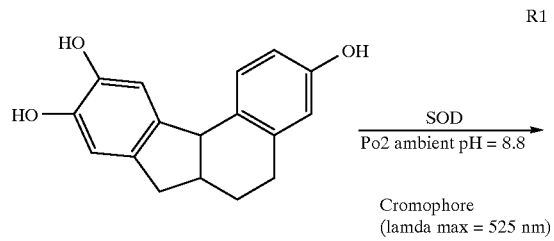

The SOD-525 method also exploits a second reactant, R2, which allows the elimination of major interferences due to mercaptans which could be present in the sample to be analysed, such as, for example glutathion, with the aid of a very rapid alkylation reaction, according to the reaction:

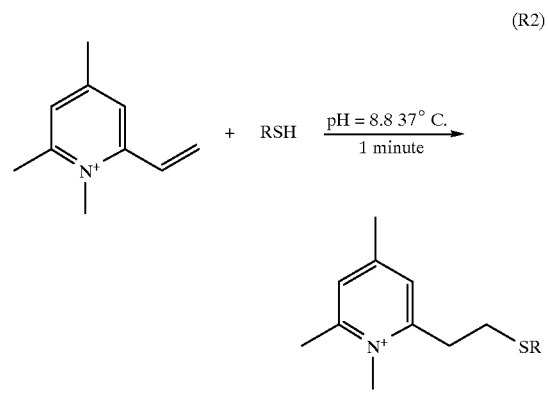

The measurement of the SOD activity is carried out at a pH of 8.8, which allows for an optimal sensitivity of the determination without inactivating the known natural SODs, such as, for example the copper-zinc SODs, manganese or iron SODs.

There is a determination kit, commercialized by Oxis International S. A., (94385 Bonneuil sur Marne, France), which allows carrying out a spectrophotometric determination of SOD activity by this SOD-525 method. This kit comprises two reactants, R1 and R2, and a buffer solution, buffer 3, which are respectively:

R1: a solution of chromogenic reagent R1 of the above-mentioned formula in 3.2 $10^{-2}$M HCl;

R2: a solution of mercaptan trapping reagent R2 in DMSO containing 25% (w/v) ethylene glycol;

buffer 3: a buffer of pH=8.8 (at 37° C.) containing 0.11 mM diethylene triamine pentaacetic acid (DTPA).

With this Oxis International kit, commercialized under the name of SOD-525 kit, the spectrophotometric determinations are carried out in glass cells of 1 cm of optical path, at a wavelength of 525 nm. The kinetic measurement of the evolution of the absorbance is carried out for 1 minute at 37° C.

For each measurement, the reaction rate is determined by evaluating the maximal slope of the curve obtained. This slope corresponds to an auto-oxidation phase of R1. The results are expressed in units of absorbance per minute.

The calculation of the enzymatic activity is effected as follows: $V_c$ and $V_s$ are the reaction rates corresponding respectively to the control and the sample. The SOD activity of the sample to be analysed is determined by calculating the correspondence between the experimental ratio $V_s/V_c$ and the SOD activity, deduced from the following equation:

$$\frac{V_s}{V_c} = 1 + \frac{[SOD]}{a[SOD]+b} \text{with } a = 0.073 \text{ and } b = 0.93 \qquad [1]$$

One unit of SOD-525 activity defined by Oxis corresponds to a $V_s/V_c$ ratio equal to 2 under the above conditions.

The value obtained is then multiplied by the dilution factor of the sample (factor 25) in the determination method. The results are expressed in units of SOD-525 activity per ml of sample.

In the framework of the invention, the enzymatic activity of SOD is measured after dilution of the SOD solution obtained in order to remain in the $V_s/V_c$ ratio values allowing establishing a correct correspondence with the SOD activity.

In the framework of the invention, the SOD solution obtained is generally diluted, as a function of the degree of purification resulting from the exctraction method up to a factor of 300, in order to obtain a $V_s/V_c$ ratio comprised between 1 and 2.

The activity of the SOD solution is determined by taking into account the dilution factor of the sample of the determination procedure (factor 25) and the dilution factor of the SOD solution itself (for example up to a factor of 300).

The examples of determination will be given in relation with the examples.

The invention further covers compositions notably with anti-free radical activity, for example cosmetic, pharmaceutical or food compositions characterized in that they comprise as one of the active ingredients a plant SOD obtained from plant seeds having undergone a germination step.

In this third aspect, the proportion of incorporation is variable and depends upon the envisaged use. Generally, the proportion of incorporation of SOD will be from 0.01 to 30% by weight, better from 0.1 and 10% by weight and even better in the order of 1 to 5%.

In an advantageous embodiment of this comosition, SOD is present in the form of SOD/peroxidase complex with preferably a peroxidase cofactor known as peroxidase specific reducing substrate.

Peroxidases catalyse the destruction of hydrogen peroxide ($H_2O_2$) produced during the dismutation reaction catalysed by SOD of the superoxide anion to give hydrogen peroxide, as given at the beginning of the desription in the presence of a specific reducing substrate (peroxidase cofactor).

Peroxidases are numerous and are well known to the person skilled in the art. They are currently extracted from the spinal cord (myelo-peroxidase), from milk (lactoperoxidase), from bovine or optionally human red blood corpuscles (glutathion peroxidase) or even preferably in the invention from black radish (horseradish peroxidase).

Furthermore, the specific reducing substrates of the peroxidases are well known to the person skilled in the art and are preferably selected from glutathion, phenol, guaiacol, pyrogallol, mesitol, 3,5-dichloro-2-hydroxybenzenesulfonic acid (DCHBS), aniline, p-toluidine, o-phenylene diamine, mesidine, ascorbic acid, dihydroxymaleic acid, cytochrome C, iodides, uric acid, phenolphthalein, 2,2'-azido-di(3-ethylbenzothiazoline-6-sulfonic) acid (ABTS) and compounds such as $SCN^-$, $Cl^-$, $Br^-$ or $I^-$.

In the framework of the invention, and notably for an application in cosmetics, pharmaceuticals or in food, it is preferable to prepare a complex of SOD with a plant peroxidase preferably extracted from black radish, advantageously accompanied by its cofactor, constituted preferably by uric acid, ascorbic acid or dihydroxymaleic acid.

The amount of peroxidase added to the SOD is a function of the amount of hydrogen peroxide released by SOD, therefore of its enzymatic activity. The number of units of peroxidases to be added to the SOD solution is expressed in a ratio of units of peroxidase to the units of SOD in the invention is about 10/400.

The enzymatic cofactor of the peroxidase such as described previously, which can be preferably uric acid, is added to the enzymatic complex at a concentration comprised between 0.001M and 1M with respect to the SOD/peroxidase complex.

In a preferred implementation variant of the invention, SOD or the SOD/peroxidase/peroxidase cofactor complex can be further stabilized by at least a sugar and/or at least a polyol added at a concentration comprised between 10 and 50% by weight of SOD or of the final complex, in the form of crude extract or in purified form.

As a sugar, a monosaccharide or a disaccharide can be used in particular, and especially trehalose, and as a polyol a polyol having an average molecular weight comprised between 50 and 1000 g/mole can be used in particular, for example, glycerol, sorbitol, maltitol and mannitol. The addition of a sugar or a polyol allows the stabilization of the SOD in a particularly unexpected manner.

Furthermore, in yet another preferred embodiment of the invention, an advantageously lipophilic anti-oxidizing agent is added, preferably one from the tocopherol family and their derivatives, such as their esters, such as acetates, linoleates or even phosphates, since it has been discovered in a particularly unexpected manner that such an anti-oxidizing agent procures a greater stability of SOD. Tocopherol phosphates are, for example, described in the U.S. Pat. No. 5,387,579 of LVMH Recherche. This result is particularly unexpected since the stability of the SOD enzyme is not linked to problems of oxidation, and from this fact the mechanism of action is so far unknown. Given that this anti-oxidizing agent is advantageously lipophilic, it is added to the composition in an oily phase, i.e. in general by way of formation of an emulsion. The concentration of anti-oxidizing agent is generally from 0.01 to 3%, preferably from 0.1 to 1% by weight with respect to the total weight of the final composition.

According to a fourth aspect, the present invention provides a method of treatment of a mammal against the harmful effects of free radicals especially in inflammation by administering SOD extracted from germinated plant seeds in an amount effective against free radicals.

According to a specific embodiment, said treatment method comprises administering a composition comprising from 0.01 to 10% by weight of SOD extracted from germinated plant seeds.

According to a further specific embodiment of said treatment method, said mammal is a human.

Other aims, characteristics and advantages of the invention will appear clearly in the light of the description which follows made with reference to several examples of implementation of the invention given simply in an illustrative manner and which in no way limit the scope of the invention. In the examples, all the proportions are given by weight unless otherwise stated.

The examples are an integral part of the invention and any characteristic of the examples which would appear novel with respect to any state of the art constitutes a general characteristic of the invention claimed in as such.

EXAMPLE 1

Extraction of SOD from Germinated Barley

This extraction of SOD takes place in the following manner:

a) Germination of the Barley:

Commercially available barley is taken, for example the spring barley variety Dallas, and is soaked in an aqueous solution, for example tap water or preferably demineralized water, in the cold, for example 15° C., for one or more days, for example two days.

After soaking, which has as aim to swell the seeds, and thus to prepare the germination, the step properly called the germination step is carried out for several days, for example five days, preferably in the presence of a germination-favoring agent, such as gibberellic acid at a concentration of 0.1 mg/kg of dry starting grains.

b) Extraction Protocol:

The protocol of extraction from the germinated barley, known also as malt, is the following:

After germination of the barley seeds, the malt is ground, then extracted with an aqueous buffer solution having a pH in the order of 8, which is preferably constituted by 50 mM Tris HCl+1 mM EDTA, for about 1 hour at ambient temperature.

The extract is then filtered in order to remove the husk, centrifuged at 4000 G for 20 minutes in order to remove the polysaccharide part, and the filtrate or supernatant is recovered on which the SOD activity is determined by the above-mentioned method of Nebot C., et al. (1993) with the aid of the commercial kit from Oxis International, 94385 Bonneuil sur Marne, France. A SOD-525/g activity of the dry starting material is obtained.

The SOD activity is measured after dilution of 1 ml of the SOD extract in 14 ml of water. 40 μl of the diluted solution is determined. The measured $V_s/V_c$ ratio is 1.95. From the above-mentioned equation (1), page 8, the SOD activity is 0.95 SOD-525 units. The SOD activity is therefore equal to 0.95×25×15=356,25 SOD-525 units/ml making in this example 1482 SOD-525 units/g of dry starting material.

c) Supplementary Purification:

The filtrate or supernatant obtained from the above centrifugation is submitted to a precipitation by a precipitating agent which removes the undesirable proteins such as proteases or even lipoxygenase, for example ammonium sulfate at a concentration of 390 g/l.

Centrifugation at 4,000 G is carried out for 20 minutes at 20° C. in order to remove the precipitate and the liquid fraction constituted by the supernatant which contains SOD is recovered.

The supernatant can advantageously be dialysed in order to remove small molecules and salts present in a high concentration having a molecular weight lower than 6000 Daltons. This dialysis is carried out against demineralized water with membranes whose cut-off threshold is 6,000–8,000 Daltons, for example 6,000 Daltons. In fact, the SOD has a molecular weight in the order of 30,000, which does not pass through the pores of such membranes, which allows increasing the specific activity of the enzyme.

The measured SOD activity on the dialysate according to the previous method is 7,500 SOD-525 units/g of dry starting material.

d) Optional Supplementary Purification by Column:

From the dialysate obtained in step c) above, it is even possible to carry out a purification which is much more complete by working on a chromatographic column.

A chromatography can, for example, be carried out on a Sephadex QAE column, which has allowed the purification of SOD and the removal of all protein contamination of the extract.

EXAMPLE 2

Extraction of SOD from Soya Seeds

The method described in Example 1 is carried out.

A SOD activity of 180 $IU_{SOD}$/g of the dry starting material is obtained after step b.

EXAMPLE 3

Extraction of SOD from Germinated Wheat Grains

The same protocol as that described in example 1 is used and the SOD activity is measured on the product of extraction of step b and a SOD activity of 116 $IU_{SOD}$/g of dry starting material is obtained.

EXAMPLE 4

Extraction of SOD from Germinated Peas

Commercially available white peas (*Pisum sativum*) are used.

The same protocol as that described in example 1 is used and a SOD activity is measured on the product obtained in step b. A SOD activity of 80 $IU_{SOD}$/g fo the dry starting material is obtained.

EXAMPLE 5

Determination of the Variation of the SOD Activity at Different Germination Times or with Different Barley Varieties in the Presence or not of a Germination Activating Agent such as a Molecule Belonging to the Gibberellin Family

EXAMPLE 5-a

Determination of the Variation of the SOD Activity at Different Germination Times The SOD activity is determined from the Dallas variety of germinated barley in varying the time of germination and in respecting the other general conditions of the germination protocols of example 1-a.

The results indicated in the Table I below are obtained.

TABLE I

| SOD activity in $IU_{SOD}$/g of dry material | Germination time (days) |
|---|---|
| 50 | 1 |
| 120 | 2 |
| 290 | 3 |
| 410 | 4 |
| 480 | 5 |

It is noted from the results of Table I that the SOD activity is more than doubled after 1 day of germination and that the activity is more than doubled again after the third day of germination and that the activity increases again in a considerable manner on the fourth and fifth days.

EXAMPLE 5-b

Determination of the Influence of the Variety of Barley on the SOD Activity

The influence of the variety of barley on the SOD activity has been determined and the results obtained are given in Table II below. This comparison has been carried out at a constant germination time of 5 days but without a germination-favorizing agent, the other conditions of the germination protocol being identical to that of example I-a.

TABLE II

| Variety of barley | SOD activity in $IU_{SOD}$/g of dry material |
|---|---|
| Natasha | 239 |
| Felicie | 271 |
| Dallas | 214 |
| Magie | 218 |
| Puffin | 247 |

It is noted from Table II that a slight variation in the results obtained in SOD activity exists for various barley varieties but that these results are in perfect agreement, which proves the reproducibility of the germination method according to the present invention.

EXAMPLE 5-c

Influence of the Presence of a Molecule of the Gibberellin Family

The influence of the presence of a germination favoring agent, such as gibberellic acid, has also been determined and the results are given in Table III. These experiments have been carried out on spring barley (Natasha variety) according to the protocol of example 1 with a germination time of 5 days.

TABLE III

| Gibberellic acid | SOD activity in $IU_{SOD}$/g of dry material |
|---|---|
| without | 239 |
| with 0.1 mg/kg of grains | 407 |

It can be noted from table III that the presence of a germination favoring agent allows increasing the quantity of SOD produced in a particularly unexpected manner.

EXAMPLE 6

Stabilization of the SOD by a Polyol

The SOD in the form of crude extract obtained in example 1 step b) retains 60% of its enzymatic activity after 46 days at 20 C.

11

It has been noted that if one adds to the crude extract 20% by weight of sorbitol with respect to the final solution of this crude extract, i.e. SOD extract of step 1-b plus 20% sorbitol by weight of the final solution, the stability of the SOD enzyme is increased in an unexpected manner and that 76% of the initial activity is recovered after 46 days at 20° C.

EXAMPLE 7

Stabilization of the SOD by a Sugar

It has been discovered that the enzymatic activity of the SOD could be stabilized by the addition of a sugar preferably a monosaccharide or a disaccharide. In this example, trehalose is used.

If one proceeds as described in example 6, but one adds 30% by weight of trehalose to the crude SOD extract obtained in example 1 step b), with respect to the weight of the final solution, it is noted that 75% of the initial activity is recovered after 46 days at 20° C., which constitutes a remarkable increase in stability.

EXAMPLE 8

Stabilization of the SOD by a Peroxidase and a Cofactor

The concentrated solution of SOD obtained in step 1-d or obtained in a prior step of example 1 is complexed to or combined with another enzyme capable of destroying the hydrogen peroxide formed.

The enzymes which can be used in this sense can be a catalase which converts $H_2O_2$ into $H_2O$ and $O_2$ but catalase is not used insofar as it belongs to the list of non-authorized products in cosmetics. A peroxidase can also be used which also catalyses the destruction of $H_2O_2$ which necessitates nevertheless the presence of a specific reducing substrate or cofactor. The lists of peroxidases and cofactors have been given in the introduction to the description.

In the framework of this example, a plant peroxidase extracted from black radish (or horseradish peroxidase), hereinafter given as the abbreviation HRP, is used as peroxidase, combined with an enzymatic cofactor constituted by uric acid.

In the framework of this example, the amount of peroxidase added to the SOD is about 10 units of peroxidases for 400 units of SOD, the SOD unit being determined according to the method previously described and the unit of peroxidase being determined by the method described by Bergmeyer H. U. in Methods of Enzymatic Analysis (1974), vol. 1, $2^{nd}$ ed., page 494.

The enzymatic cofactor of the peroxidase constituted here by uric acid is added to the SOD/peroxidase enzymatic complex in a concentration comprised between 0.01 and 1M, preferably 0.5M.

Preferably, the complex thus formed is further stabilized by the addition of sugar or polyol added at a concentration selected in this example of 30% by weight of the final solution.

This SOD/peroxidase/cofactor complex can be used as it is for the formulation of the compositions with anti-radical activity or free radical trapping activity, be it cosmetic, pharmaceutical or food compositions or others. This complex is also the subject of stability, anti-radical capacity and toxicology tests, the subject of examples 9, 10 and 11 respectively, below.

12

EXAMPLE 9

Stability Tests

The stability of the enzymatic activity of the complex formed in example 8 has been effected at 20° C. and 45° C. respectively and the results obtained are given in Table IV below.

TABLE IV

| Days | SOD activity SOD-525 units/ml 20° C. | SOD activity SOD-525 units/ml 45° C. |
|---|---|---|
| 0 | 5025 | 5025 |
| 7 | 4800 | 4275 |
| 11 | 7575 | 3575 |
| 13 | 5925 | 3150 |
| 18 | 4500 | 2800 |
| 20 | 2475 | 2400 |
| 35 | 3975 | 2475 |

It emerges from Table IV that the enzymatic activity is stable at 20° C. for 1 month, since at 35 days 80% of the enzymatic activity is retained, while at 45° C. a drop in activity in the order of 50% is obtained, which represents a remarkably small drop in activity for an enzyme at this temperature.

It is thus observed that this plant SOD/peroxidase/cofactor complex possesses a remarkable stability, particularly at 45° C., which is unexpected for a person skilled in the art.

EXAMPLE 10

Determination of the Anti-radical Activity or Free Radical Trapping Activity

1°. 3 methods of evaluation in vitro of radical trapping have been used:

a) the first method uses an enzymatic system constituted by xanthine oxidase which, in oxidizing its substrate, xanthine, generates superoxide radicals. The latter are capable of reducing cytochrome C ($Fe^{3+}$) into cytochrome C ($Fe^{2+}$), a reaction whose kinetics can be followed by UV-visible spectrophotometry at 550 nm. They are also the radical substrates of the SODs which can also enter in competition with the cytochrome C for the capture and the elimination of superoxide radicals. By adding a preparation containing a SOD activity, these kinetics of reduction are slowed down. The calculation of the SOD activity is effected by the calculation of the percentage inhibition of the reduction of the cytochrome C by the SOD under test.

One SOD unit expressed in the international system (1 $IU_{SOD}$) corresponds to the activity necessary for decreasing by 50% the level of reduction of the cytochrome C, at a temperature of 25° C. and at a pH of 7.8.

The sample to be tested is diluted in a way as to determine the conditions for which a 50% inhibition of the reduction of cytochrome C is obtained, corresponding to 1 international system unit.

The total SOD activity of the sample tested is then determined in taking the volume of the sample determined up to the total volume of the sample and in taking into account the initial dilution factor of the sample.

The SOD activity of the complex formed in example 8 determined by this method is 4,455 $IU_{SOD}$ units/ml.

b) The second method is constituted by a determination kit commercialized by Oxis International, under the commercial name SOD-525 kit, based on the property that any catalyst with a SOD activity can accelerate the auto-oxidation of a tetracyclic catechol derivative (5,6,6a,11b-tetrahydro-3,9,10-trihydroxybenzofluorene).

This determination method allows determining the SOD activity in the form of SOD-525 units which are defined as the amount of dismutase which multiplies by 2 the level of oxidation of the catechol derivative.

The SOD activity of the complex formed in example 8, determined by this method, is 4,375 SOD-525 units/ml.

It is thus noted that the values of the SOD activity obtained by these two methods are essentially identical.

c) The third method used is electron spin resonance, abbreviated to ESR.

ESR is a technique which allows the characterization of the spin states of single electrons of molecules, more particularly used for the characterization of free radicals. The evaluation of the anti-radical activity of the SOD/peroxidase/cofactor complex obtained in example 8 by ESR allows distinguishing the superoxide and hydroxyl radical trapping activity (Rosen G. M. and Rauckman E. J. in Methods in Enzymology (1984), 105, pages 198–209).

The very short lifetime of the free radicals, about $10^{-11}$ seconds for OH·, limits the ability to detect the latter. For this reason, the $O_2·^-$ and OH· radicals are observed with the aid of a spin-trap. This molecule resonates in the presence of free radicals and stabilizes them in the form of complexes which possess a characteristic spectrum detectable by ESR.

The trapping effect of a product of the test is directly evidenced by a decrease in the intensity of the signal emitted by the spin-trap molecule.

The ESR determinations are carried out on a Brücker ESP 106 spectrometer, at room temperature; the spin-trap used is 5,5-dimethyl-1-pyrroline-N-oxide (DMPO).

The superoxide anion is produced by the xanthine (1.5 mM)/xanthine oxidase (12 mU/ml) enzymatic system, in the presence of DMPO (80 mM) and 50% (v/v) ethanol. The SOD/peroxidase/cofactor complex obtained in example 8 is dissolved in ultrapure water at various concentrations.

The hydroxyl radical is produced by photolysis (UVB) of 0.2% (v/v) hydrogen peroxide in aqueous solution, in the presence of DMPO (160 mM). The SOD/peroxidase/cofactor complex obtained in example 8 is dissolved in ultrapure water at various concentrations.

The ESR signal intensities are calculated by double integration of the lowest field spectral line. The percentages of protection of the product under test are obtained from the blank values without test product.

$$\% \text{ protection} = \left[\frac{S_{product} - S_{blank}}{S_0 - S_{blank}}\right] \times 100$$

$S_{product}$: integration of the ESR signal obtained with the test compound or the reference $S_{blank}$: integration of the ESR signal obtained with the blank $S_0$: integration of the ESR signal obtained in the absence of free radicals

Effect on the Superoxide Radical

The SOD/peroxidase/cofactor obtained in example 8 decreases the ESR signal of the superoxide anion in a dose-dependent manner. At 5 and 10% (v/v), the complex inhibits the ESR signal by 44% and 54%.

Effect on the Hydroxyl Radical

The SOD/peroxidase/cofactor complex obtained in example 8 decreases the ESR signal of the hydroxyl radical in a dose-dependent manner. At the concentration of 0.3% (v/v), the effect is spectacular since it inhibits the ESR signal by 93%.

The SOD/peroxidase/cofactor complex obtained in example 8 possesses very interesting anti-radical effects on the superoxide anion and the hydroxyl radical even at weak concentrations, generally employed in cosmetic compositions.

2°. A method of evaluation ex vivo of the anti-radical activity has been used on normal human fibroblasts in culture.

After irradiation with UVA, the free radicals formed in a culture of human fibroblasts are quantified by an appropriate method. The utilization of anti-radical agents allows decreasing the oxidative stress, and the calculation of the efficiency of the plant SOD/peroxidase/cofactor complex according to example 8 at different concentrations is effected.

Normal human fibroblasts are incubated for 1 hour in the presence of the plant SOD/peroxidase/cofactor complex of example 8, tested at 0.01, 1 and 10% (v/v) in demineralized water. The cells are submitted to a radical stress provoked by luminous UVA rays (10 J/cm$^2$). The free radicals formed (hydroperoxides) are detected with the aid of an appropriate probe, which transforms itself in the presence of hydroperoxides, into a quantifiable fluorescent derivative.

The results are first of all expressed in arbitrary units of fluorescence per culture pit. Then an efficiency is calculated by applying the following formula:

$$E(\%) = [(ITF-IF)/(IF-NIF)] \times (-100)$$

wherein:

E: Percentage efficiency

NIF: Fluorescence observed with Non Irradiated Fibroblasts

IF: Fluorescence observed with Irradiated Fibroblasts

ITF: Fluorescence observed with Irradiated and Treated Fibroblasts

An aqueous solution containing 1% of plant SOD/peroxidase/cofactor complex formed according to the invention is capable of reducing more than 80% of the harmful effects linked with an oxidative stress generated by the UVA rays.

This efficiency is greater than that obtained with the reference mixture glutathion/vitamin C nevertheless recognized as being particularly efficient, but which moreover presents enormous stability problems.

From the weakest concentrations of use, the plant SOD/peroxidase/cofactor complex according to example 8 allows therefore an efficient protection of human fibroblasts, cultivated after an oxidative stress by UVA rays.

3°. The method of evaluation in vivo of the anti-radical activity has been used on the cutaneous tissues of healthy volunteers.

The free radicals formed following UVA irradiation peroxidize the unsaturated lipids of the cutaneous tissues. The strippings allow the removal of the corneocytes with the peroxidized entities. In the reaction medium, the peroxides are visualized with the aid of a fluorescent probe which emits a fluorescence directly proportional to the level of peroxides present.

Seven female volunteers, aged between 20 and 38 possessing a II or III phototype, i. e. possessing a normal Caucasian skin are selected.

Three zones of the forearm are defined and two of these zones are irradiated with UVA (10 J/cm$^2$). with the aid of a UVA Sun 3000S® lamp. The transient red mark obtained is not visible the day after the irradiation and no inflammatory process is observed.

An aqueous solution containing 1% of the plant SOD/peroxidase/cofactor formed according to the invention is applied 4 times at two hour intervals (2 µl/cm²).

24 hours after the irradiation with UVA, a sampling of the horny layer is taken by two successive strippings.

The peroxides formed are visualized on the second stripping with the aid of a fluorescent probe which gives a general response on the peroxidation process.

The results are firstly expressed in arbitrary units of fluorescence. Then an efficiency is calculated by applying the following formula:

$$E(\%)=[(TIZ-IZ)/(IZ-NIZ)]\times(-100)$$

wherein:

E(%): Percentage efficiency

TIZ: Fluorescence measured on the Treated Irradiated Zone

IZ: Fluorescence measured on the Irradiated zone

NIZ: Fluorescence measured on the Non Irradiated Zone.

An aqueous solution containing 1% of the plant SOD/peroxidase/cofactor complex formed according to the invention is capable of protecting, with an efficiency of 65%, the cutaneous radical stress induced by a UVA irradiation.

EXAMPLE 11

Toxicology

The toxicology experiments have been carried out on the complex according to the invention obtained in example 8 on the evaluation of the cutaneous first irradiation in the rabbit (9a), on the evaluation of the ocular irritation in the rabbit (9b), on the absence of abnormal toxicity by single oral administration in the rat (9c) and by the study of the sensitizing power on the guinea pig (9d).

11a—Evaluation of the Cutaneous First Irradiation in the Rabbit

The preparation obtained in example 8 was applied without dilution at the dose of 0.5 ml on the skin of 3 rabbits according to the method recommended by the OECD directive No. 404 concerning the <<irritant/acute corrosive effect on the skin>> study.

The results of this study have allowed concluding that the preparation obtained in example 8 according to the invention can be considered to be a non-irritant even in the non-diluted state.

11b—Evolution of the Ocular Irritation in the Rabbit 0.1 ml of the same preparation obtained in example 8 has been instilled pure, once only, in the eye of three rabbits according to the method recommended by the OECD directive No. 405 of 24$^{th}$ February 1987 concerning the <<irritant/acute corrosive effect on the eyes>> study.

The results of this test allow concluding that the preparation obtained in example 8 according to the invention can be considered as being non-irritant to the eyes, in the sense of the directive 91/326 EEC, utilized pure or without dilution.

11c—Test on the Absence of Abnormal Toxicity by Single Oral Administration in the Rat The preparation obtained in example 8 according to the invention was administered once via the oral route at the dose of 5 g/kg of body weight, to 5 male rats and 5 female rats according to a protocol inspired by the directive of the OECD No. 401 of 24$^{th}$ February 1987 and adapted to cosmetic products.

The results of this test allow concluding that, under the experimental conditions, the preparation obtained in example 8 according to the invention do not possess any abnormal toxicity.

11d—Study of Sensitizing Power in the Guinea Pig

The SOD complex solution obtained in example 8 was the subject of sensitizing power investigation according to the method of Magnusson and Kligman published in J. Invest. Derm. (1969), 52, pages 268–276. This solution of SOD complex was applied as such to the skin of 35 guinea pigs treated beforehand with Freund's adjuvant and divided into 2 experimental batches, reference batch and treated batch respectively.

No reaction was noted in the two experimental batches.

The results obtained show that the plant SOD/peroxidase/cofactor complex formed according to the invention does not provoke the appearance of any sensitization reaction.

EXAMPLE 12

Preparation of a Composition in the Form of a Cosmetic Emulsion Containing the Plant SOD/peroxidase/cofactor Preparation According to the Invention The preparation obtained in example 8 according to the invention is incorporated in a cream at a concentration of 5% by weight with respect to the total weight of this cream.

This cream has the following composition:

| INCI name | |
|---|---|
| A- Steareth-2 | 3% |
| Steareth-21 | 2% |
| Propylene glycol-15 stearyl ether | 9% |
| Cetearyl alcohol | 2.5% |
| B- Butylene glycol | 4.5% |
| Water | 73.3% |
| C- Preservative comprising parabens and phenoxyethanol | 0.5% |
| D- Tocopherol | 0.2% |
| E- Plant SOD/peroxidase/cofactor complex according to the invention of example 8 | 5% |

The enzymatic activity in the cream is determined after a separation of the aqueous and oily phases, carried out in specific conditions: 2 g of cream are diluted 5 times in 8 g of 0.2M Tris(hydroxymethyl)aminomethane buffer pH 8.5, then 10% of NaCl are added. The mixture is submitted to a violent stirring (of the type obtained with the aid of an Ultra-turax) for 5 minutes then centrifuged at 5000 r/minute for 25 minutes. The enzymatic activity is determined directly in the aqueous phase extracted.

The stability of the enzymatic activity of the preparation obtained in example 8 incorporated in a cream, whose description is given above, has been studied at 20° C. and 45° C. for 40 days.

The results are given in Table V.

TABLE V

| Days | SOD activity of SOD complex stabilized according to the invention obtained in example 8 (%) 20° C. | SOD activity of SOD complex stabilized according to the invention obtained in example 8 (%) 45° C. | SOD activity of the crude SOD of extraction obtained in example 1 step b) (non-stabilized) (%) 45° C. |
| --- | --- | --- | --- |
| 0 | 100 | 100 | 100 |
| 1 | 100 | 100 | 0 |
| 3 | 89 | 83 | 0 |
| 6 | 69 | 83 | 0 |
| 18 | 92 | 64 | 0 |
| 25 | 70 | 66 | 0 |
| 40 | 60 | 50 | 0 |

The enzymatic activity recovered in the cream after 40 days at 20° C. is 60% stabilized SOD form. Even more remarkably, the enzymatic activity recovered in the cream stored for 40 days at 45° C. is 50%, while the non-stabilized form does not resist at this temperature.

The stability studies of the complex according to the invention, incorporated in a cream, show that the complex possesses a remarkable stability at 20° C. and a particularly unexpected stability at 45° C.

EXAMPLE 13

Preparation of the Plant SOD Complex with Various Peroxidases

EXAMPLE 13A

SOD Complex/horseradish Peroxidase

The solution of SOD obtained in step 1c of example 1 is used in which a nits of horseradish plant peroxidase (HRP) is introduced in a ratio of th respect to the SOD units comprised between 10 and 400.

The preparation of plant SOD/horseradish peroxidase thus obtained can be used as such or preferentially combined with an enzymatic cofactor, for example uric acid, ascorbic acid or dihydroxymaleic acid.

EXAMPLE 13B

Plant SOD/Arthromyces Ramosus Peroxidase Complex

Carried out as in example 13A except a peroxidase obtained from commercially available Arthromyces ramosus, under the reference Sigma P 4794, is used.

EXAMPLE 13C

Plant SOD/Soya Peroxidase Complex

Carried out as described in example 13A except a peroxidase extracted from commercially available soya under the reference Sigma P1462, is used.

EXAMPLE 14

Stabilization of the Plant SOD/peroxidase/cofactor Complex with a Sugar or Polyol The stabilization is increased of the plant SOD/peroxidase/cofactor enzymatic complex obtained in example 8 by the addition at least of a sugar or polyol according to the following implementation variants:

EXAMPLE 14A

Addition of Glycerol

In the preparation obtained in example 8 according to the invention, glycerol is added at a concentration selected in this example of 30% by weight of the final solution, with stirring at room temperature.

EXAMPLE 14B

Addition of Sorbitol

Carried out as in example 14A, except sorbitol is used.

EXAMPLE 14C

Addition of Maltitol

Carried out as in example 14A, except maltitol is used.

EXAMPLE 14D

Addition of Mannitol

Carried out as in example 14A, except mannitol is used.

EXAMPLE 14E

Addition of Trehalose

Carried out as in example 14A, except trehalose is used.

EXAMPLE 15

Formation of the Enzymatic Complex with Different Peroxidase Cofactors

Carried out as described in example 8, except peroxidase cofactors other than uric acid are used, uric acid being used in example 8.

EXAMPLE 15A

Ascorbic Acid

Carried out as described in example 8, except ascorbic acid is used in the place of uric acid at a concentration comprised between 0.01 and 1M, preferably 0.5M.

EXAMPLE 15B

Dihydroxymaleic Acid

Carried out as described in example 8, except dihydroxymaleic acid is used instead of uric acid, at a concentration comprised between 0.01 and 1M, preferably 0.5M.

EXAMPLE 16

Cosmetic Composition, of Oil-in-water Emulsion Type, Usable most Particularly for the Anti-radical Cosmetic Preparations, for Anti-age, Anti-wrinkles and Anti-stress of the Skin A composition in the form of oil-in-water emulsion is prepared in a classical manner from the following five fractions A, B, C, D and E having the centesimal composition indicated:

| INCI name | |
|---|---|
| A- Oily phase comprising | |
| Steareth-2 | 3% |
| Steareth-21 | 2% |
| Propylene glycol-15 stearyl ether | 9% |
| Cetearyl alcohol | 2.5% |
| B- Butylene glycol | 4.5% |
| Water | 73.3% |
| C- Preservative comprising parabens and phenoxyethanol | 0.5% |
| D- Tocopherol | 0.2% |
| E- Plant SOD/peroxidase/cofactor complex according to the invention of example 8 | 5% |

After having heated the greasy and aqueous phases at 80° C. separately, phase B is mixed in with phase A, then phase C, phase D and then phase E until an oil-in-water emulsion is obtained.

EXAMPLE 17

Pharmaceutical Composition with Anti-inflammatory Activity

This pharmaceutical composition comprises, as well as a classical pharmaceutical active ingredient, a preparation such as obtained in example 8 according to the invention, 5% by weight in a mixture with a pharmaceutically acceptable excipient.

EXAMPLE 18

Food Composition Stabilized Against Oxidation

This food composition possesses a stability against rancidness and 20 comprises, besides the classical food active ingredients, 5% by weight of preparation obtained in example 8 according to the invention which are incorporated at the same time as the other active ingredients.

We claim:

1. A composition comprising superoxide dismutase (SOD) stabilized by an $H_2O_2$ trapping agent comprising a peroxidase with a peroxidase cofactor as peroxidase specific reducing substrate, said SOD being further stabilized by the addition of a hydrophilic substance selected from the group consisting of a sugar and a polyol having a molecular weight of not more than 2,000 g/mole, thereby providing SOD heat stability at a temperature of at least about 45° C.

2. The composition of claim 1, wherein said sugar or polyol is present at a concentration ranging between 10 and 50% by weight of SOD component selected from the group consisting of SOD and of SOD/peroxidase/peroxidase cofactor.

3. A composition comprising superoxide dismutase (SOD) stabilized by an $H_2O_2$ trapping agent comprising a peroxidase with a peroxidase cofactor as peroxidase specific reducing substrate, said SOD being further stabilized by the addition of a sugar selected from the group consisting of a monosaccharide and a disaccharide, thereby providing SOD heat stability at a temperature of at least about 45° C.

4. The composition of claim 3, wherein said sugar is trehalose.

5. The composition of claim 3, wherein said sugar is present at a concentration ranging between 10 and 50% by weight of SOD component selected from the group consisting of SOD and of SOD/peroxidase/peroxidase cofactor.

6. The composition of claim 3, wherein said SOD is present at a concentration ranging from 0.01 to 10% by weight with respect to the total weight of the composition.

7. The composition of claim 3, wherein the amount of peroxidase added to the SOD, expressed in a ratio of peroxidase units with respect to SOD units, is 10/400.

8. The composition of claim 3, wherein the peroxidase cofactor is present at a concentration between 0.001M and 1M.

9. The composition of claim 3, wherein the peroxidase is selected from the group consisting of a horseradish peroxidase, a lactoperoxidase, a glutathione peroxidase, and a spinal cord peroxidase.

10. The composition of claim 3, wherein the peroxidase cofactor is selected from the group consisting of glutathione, phenol, guaiacol, pyrogallol, mesitol, 3,5-dichloro-2-hydroxybenzenesulfonic acid (DCHBS), aniline, p-toluidine, o-phenylene diamine, mesidine, ascorbic acid, dihydroxymaleic acid, cytochrome C, an iodide, a chloride, a bromide, uric acid, phenolphthalein, 2,2'-azido-di(3-ethylbenzo-thiazoline-6-sulfonic acid (ABTS), and $SCN^-$.

11. The composition of claim 3, wherein the peroxidase is a plant peroxidase.

12. The composition of claim 11, wherein the plant peroxidase is extracted from black radish.

13. The composition of claim 3, wherein the peroxidase cofactor is selected from the group consisting of uric acid, ascorbic acid, and dihydroxymaleic acid.

14. The composition of claim 3, further comprising a lipophilic antioxidant, which is a tocopherol selected from the group consisting of tocopherol, tocopherol acetate, tocopherol linoleate, and tocopherol phosphate, in an effective anti-oxidizing amount.

15. The composition of claim 3, further comprising a lipophilic antioxidant, which is a tocopherol selected from the group consisting of tocopherol, tocopherol acetate, tocopherol linoleate, and tocopherol phosphate, at concentration of 0.01 to 3% by weight with respect to the total weight of the final composition.

16. The composition of claim 3, wherein the SOD is extracted from plant seeds and is stabilized by a plant peroxidase extracted from black radish, further by a peroxidase cofactor selected from the group consisting of uric acid, ascorbic acid and dihydroxymaleic acid, and further stabilized by the addition of trehalose.

17. A composition comprising superoxide dismutase (SOD) stabilized by an $H_2O_2$ trapping agent comprising a peroxidase with a peroxidase cofactor as peroxidase specific reducing substrate, said SOD being further stabilized by the addition of a polyol having an average molecular weight ranging from 50 to 1,000 g/mole, thereby providing SOD heat stability at a temperature of at least about 45° C.

18. The composition of claim 17, wherein said polyol is selected from the group consisting of glycerol, sorbitol and mannitol.

19. The composition of claim 17, wherein said polyol is present at a concentration ranging between 10 and 50% by weight of SOD component selected from the group consisting of SOD and of SOD/peroxidase/peroxidase cofactor.

20. The composition of claim 17, wherein said SOD is present at a concentration ranging from 0.01 to 10% by weight with respect to the total weight of the composition.

21. The composition of claim 17, wherein the amount of peroxidase added to the SOD, expressed in a ratio of peroxidase units with respect to SOD units, is about 10/400.

22. The composition of claim 17, wherein the peroxidase cofactor is present at a concentration between 0.001M and 1M.

23. The composition of claim 17, wherein the peroxidase is selected from the group consisting of a horseradish peroxidase, a lactoperoxidase, a glutathione peroxidase, and a spinal cord peroxidase.

24. The composition of claim 17, wherein the peroxidase cofactor is selected from the group consisting of glutathione, phenol, guaiacol, pyrogallol, mesitol, 3,5-dichloro-2-hydroxybenzenesulfonic acid (DCHBS), aniline, p-toluidine, o-phenylene diamine, mesidine, ascorbic acid, dihyroxymaleic acid, cytochrome C, an iodide, a chloride, a bromide, uric acid, phenolphthalein, 2,2'-azido-di(3-ethylbenzo-thiazoline-6-sulfonic acid (ABTS), and SCN$^-$.

25. The composition of claim 17, wherein the peroxidase is a plant peroxidase.

26. The composition of claim 25, wherein the plant peroxidase is extracted from black radish.

27. The composition of claim 17, wherein the peroxidase cofactor is selected from the group consisting of uric acid, ascorbic acid, and dihydroxymaleic acid.

28. The composition of claim 17, further comprising a lipophilic antioxidant, which is a tocopherol selected from the group consisting of tocopherol, tocopherol acetate, tocopherol linoleate, and tocopherol phosphate, in an effective anti-oxidizing amount.

29. The composition of claim 17, further comprising a lipophilic antioxidant, which is a tocopherol selected from the group consisting of tocopherol, tocopherol acetate, tocopherol linoleate, and tocopherol phosphate, at a concentration of 0.01 to 3% by weight with respect to the total weight of the final composition.

30. The composition of claim 17, wherein the SOD is extracted from plant seeds and is stabilized by a plant peroxidase extracted from black radish, further stabilized by a peroxidase cofactor selected from the group consisting of uric acid, ascorbic acid and dihydroxymaleic acid, and further stabilized by the addition of mannitol.

31. The composition of claim 17, wherein the polyol is maltitol.

32. A composition with anti-free radical activity selected from the group consisting of a cosmetic composition, a pharmaceutical composition and a food composition, comprising as an active ingredient a plant superoxide dismutase (SOD) obtained by extraction from germinated plant seeds, said SOD being stabilized first by addition of a cosmetically, pharmaceutically or food acceptable peroxidase and peroxidase cofactor, and then by addition of a SOD stabilizing effective amount of a hydrophilic substance selected from the group consisting of a sugar and a polyol having a molecular weight of not more than 2,000 g/mole, in a cosmetically, pharmaceutically or food acceptable excipient, thereby providing SOD heat stability at a temperature of at least about 45° C.

33. The composition of claim 32, wherein said sugar or polyol is present at a concentration between 10 and 50% by weight of a SOD component selected from the group consisting of SOD and of a SOD/peroxidase/peroxidase cofactor.

34. The composition of claim 32, wherein said SOD is present at a concentration of from 0.01 to 10% by weight with respect to the total weight of the composition.

35. The composition of claim 32, wherein the amount of peroxidase added to the SOD, expressed in a ratio of peroxidase units with respect to SOD units, is about 10/400.

36. The composition of claim 35, further comprising a peroxidase cofactor present at a concentration between 0.001M and 1M.

37. The composition of claim 36, wherein the peroxidase is a plant peroxidase.

38. The composition of claim 37, wherein the plant peroxidase is extracted from black radish.

39. The composition of claim 37, wherein the peroxidase cofactor is selected from the group consisting of uric acid, ascorbic acid, and dihydroxymaleic acid.

40. A composition with anti-free radical activity selected from the group consisting of a cosmetic composition, a pharmaceutical composition and a food composition, comprising as an active ingredient a plant superoxide dismutase (SOD) obtained by extraction from germinated plant seeds, said SOD being stabilized first by addition of a cosmetically, pharmaceutically or food acceptable peroxidase and peroxidase cofactor, and then by addition of a SOD stabilizing effective amount of a sugar selected from the group consisting of a monosaccharide and a disaccharide, in a cosmetically, pharmaceutically or food acceptable excipient, thereby providing SOD heat stability at a temperature of at least about 45° C.

41. The composition of claim 40, wherein said sugar is trehalose.

42. The composition of claim 40, wherein said sugar is present at a concentration between 10 and 50% by weight of a SOD component selected from the group consisting of SOD and of a SCD/peroxidase/peroxidase cofactor.

43. The composition of claim 40, wherein said plant seeds are selected from the group consisting of cereal grains, leguminous plant seeds and oleaginous plant seeds.

44. The composition of claim 43, wherein said cereal grains are selected from the group consisting of wheat, spring barley and winter barley, said leguminous plant seeds are selected from the group consisting of lentils and peas, and said oleaginous plant seeds are Soya seeds.

45. A composition with anti-free radical activity selected from the group consisting of a cosmetic composition, a pharmaceutical composition or a food composition, comprising as an active ingredient a plant superoxide dismutase (SOD) obtained by extraction from germinated plant seeds, said SOD being stabilized first by addition of a cosmetically, pharmaceutically or food acceptable peroxidase and peroxidase cofactor, and then by addition of a SOD stabilizing effective amount of a polyol having an average molecular weight from 50 to 1,000 g/mole, in a cosmetically, pharmaceutically or food acceptable excipient, thereby providing SOD heat stability at a temperature of at least about 45° C.

46. The composition of claim 45, wherein said polyol is present at a concentration between 10 and 50% by weight of a SOD component selected from the group consisting of SOD and of a SOD/peroxidase/peroxidase cofactor.

47. The composition of claim 45, wherein the peroxidase is a plant peroxidase in an amount expressed in a ratio of peroxidase units with respect to SOD units of about 10/400.

48. The composition of claim 45, wherein said plant seeds are selected from the group consisting of cereal grains, leguminous plant seeds and oleaginous plant seeds.

49. The composition of claim 48, wherein said cereal grains are selected from the group consisting of wheat, spring barley and winter barley, said leguminous plant seeds are selected from the group consisting of lentils and peas, and said oleaginous plant seeds are Soya seeds.

50. The composition of claim 45, wherein the polyol is maltitol.

51. A cosmetic composition comprising as an active ingredient a Plant extract comprising superoxide dismutase (SOD) obtained by extraction from germinated plant seeds, said SOD being present at a concentration ranging from 0.01 to 10% by weight with respect to the total weight of the composition, a cosmetically acceptable peroxidase, a cosmetically acceptable peroxidase cofactor and a hydrophilic substance selected from the group consisting of a sugar and of a polyol having a molecular weight of not more than 2,000 g/mole at a concentration ranging between 10 and 15% by weight of SOD component selected from the group consisting of SOD and of SOD/peroxidase/peroxidase cofactor, in a cosmetically acceptable excipient, thereby providing SOD heat stability at a temperature of at least about 45° C.

52. The composition of claim 51, comprising said peroxidase cofactor acceptable in cosmetic at a concentration between 0.001M and 1M.

53. The composition of claim 51, wherein the peroxidase is a plant peroxidase in an amount expressed in a ratio of peroxidase units with respect to SOD units of about 10/400.

54. A cosmetic composition comprising as an active ingredient a plant extract comprising superoxide dismutase (SOD) obtained by extraction from germinated plant seeds, said SOD being present at a concentration ranging from 0.01 to 10% by weight with respect to the total weight of the composition, a cosmetically acceptable peroxidase, a cosmetically acceptable peroxidase cofactor and a sugar selected from the group consisting of a monosaccharide and a disaccharide, at a concentration ranging between 10 and 50% by weight of SOD component selected from the group consisting of SOD and of SOD/peroxidase/peroxidase cofactor, in a cosmetically acceptable excipient, thereby providing SOD heat stability at a temperature of at least about 45° C.

55. The composition of claim 54, wherein said sugar is trehalose.

56. The composition of claim 54, wherein said plant seeds are selected from the group consisting of cereal grains, leguminous plant seeds and oleaginous plant seeds.

57. The composition of claim 56, wherein said cereal grains are selected from the group consisting of wheat, spring barley and winter barley, said leguminous plant seeds are selected from the group consisting of lentils and peas, and said oleaginous plant seeds are Soya seeds.

58. The composition of claim 54, wherein said plant seeds are selected from the group consisting of germinated barley seeds, germinated Soya seeds, germinated wheat grains and germinated peas.

59. The composition of claim 54, wherein the peroxidase is selected from the group consisting of a horseradish peroxidase, and a glutathione peroxidase.

60. The composition of claim 54, wherein the peroxidase cofactor is selected from the group consisting of glutathione, phenol, guaiacol, pyrogallol, mesitol, 3,5-dichloro-2-hydroxybenzenesulfonic acid (DCHBS), aniline, p-toluidine, o-phenylene diamine, mesidine, ascorbic acid, dihydroxymaleic acid, cytochrome C, an iodide, a chloride, a bromide, uric acid, phenolphthalein, 2,2'-azido-di(3-ethylbenzo-thiazoline-6-sulfonic acid (ABTS), and SCN⁻.

61. The composition of claim 54, wherein the peroxidase is a plant peroxidase in an amount expressed in a ratio of peroxidase units with respect to SOD units of about 10/400.

62. The composition of claim 61, wherein the plant peroxidase is extracted from black radish.

63. The composition of claim 54, wherein the peroxidase cofactor is selected from the group consisting of uric acid, ascorbic acid, and dihydroxymaleic acid.

64. The composition of claim 54, further comprising a lipophilic antioxidant, which is a tocopherol selected from the group consisting of tocopherol, tocopherol acetate, tocopherol linoleate, and tocopherol phosphate, in an effective anti-oxidizing amount.

65. The composition of claim 54, further comprising a lipophilic antioxidant, which is a tocopherol selected from the group consisting of tocopherol, tocopherol acetate, tocopherol linoleate, and tocopherol phosphate, at a concentration of 0.01 to 3% by weight with respect to the total weight of the composition.

66. The composition of claim 54, wherein the SOD is extracted from plant seeds and is stabilized by a plant peroxidase extracted from black radish, further by a peroxidase cofactor selected from the group consisting of uric acid, ascorbic acid and dihydroxymaleic acid, and further stabilized by the addition of trehalose.

67. A cosmetic composition comprising as one of the active ingredients a plant extract comprising superoxide dismutase (SOD) obtained by extraction from germinated plant seeds, said SOD being present at a concentration ranging from 0.01 to 10% by weight with respect to the total weight of the composition, a cosmetically acceptable peroxidase, a cosmetically acceptable peroxidase cofactor, and a polyol having an average molecular weight ranging from 50 to 1,000 g/mole, at a concentration ranging between 10 and 50% by weight of SOD component selected from the group consisting of SOD and of SOD/peroxidase/peroxidase cofactor, in a cosmetically acceptable excipient, thereby providing SOD heat stability at a temperature of at least about 45° C.

68. The composition of claim 67, wherein said polyol is selected from the group consisting of glycerol, sorbitol and mannitol.

69. The composition of claim 67, wherein said plant seeds are selected from the group consisting of cereal grains, leguminous plant seeds and oleaginous plant seeds.

70. The composition of claim 69, wherein said cereal grains are selected from the group consisting of wheat, spring barley and winter barley, said leguminous plant seeds are selected from the group consisting of lentils and peas, and said oleaginous plant seeds are Soya seeds.

71. The composition of claim 67, wherein said plant seeds are selected from the group consisting of germinated barley seeds, germinated Soya seeds, germinated wheat grains and germinated peas.

72. The composition of claim 67, wherein the peroxidase is selected from the group consisting of a horseradish peroxidase, and a glutathione peroxidase.

73. The composition of claim 67, wherein the peroxidase cofactor is selected from the group consisting of glutathione, phenol, guaiacol, pyrogallol, mesitol, 3,5-dichloro-2-hydroxybenzenesulfonic acid (DCHBS), aniline, p-toluidine, o-phenylene diamine, mesidine, ascorbic acid, dihyroxymaleic acid, cytochrome C, an iodide, a chloride, a bromide, uric acid, phenolphthalein, 2,2'-azido-di(3-ethylbenzo-thiazoline-6-sulfonic acid (ABTS), and SCN⁻.

74. The composition of claim 67, wherein the peroxidase is a plant peroxidase in an amount expressed in a ratio of peroxidase units with respect to SOD units of about 10/400.

75. The composition of claim 74, wherein the plant peroxidase is extracted from black radish.

76. The composition of claim 67, wherein the peroxidase cofactor is selected from the group consisting of uric acid, ascorbic acid, and dihydroxymaleic acid.

77. The composition of claim 67, further comprising a lipophilic antioxidant, which is a tocopherol selected from the group consisting of tocopherol, tocopherol acetate, tocopherol linoleate, and tocopherol phosphate, in an effective anti-oxidizing amount.

78. The composition of claim 67, further comprising a lipophilic antioxidant, which is a tocopherol selected from the group consisting of tocopherol, tocopherol acetate, tocopherol linoleate, and tocopherol phosphate, at a concentration of 0.01 to 3% by weight with respect to the total weight of the final composition.

79. The composition of claim 67, wherein the SOD is extracted from plant seeds and is stabilized by a plant peroxidase extracted from black radish, further by a peroxidase cofactor selected from the group consisting of uric acid, ascorbic acid and dihydroxymaleic acid, and further stabilized by the addition of mannitol.

80. The composition of claim 67, comprising said peroxidase cofactor acceptable in a cosmetic at a concentration between 0.001M and 1M.

81. The composition of claim 67, wherein the polyol is maltitol.

82. A cosmetic composition comprising a germinated plant seed extract comprising superoxide dismutase (SOD), said extract being obtained by extraction from germinated plant seeds selected from the group consisting of wheat, barley, lentils, peas and Soya seeds, said SOD being present at a concentration ranging from 0.01 to 10% by weight with respect to the total weight of the composition, said SOD in said plant extract being stabilized first by addition of a cosmetically acceptable peroxidase and peroxidase cofactor and then by the addition of from 10 to 50% by weight of the total weight of the composition of a stabilizing substance selected from a monosaccharide, a disaccharide and a polyol having an average molecular weight ranging from 50 to 1,000 g/mole, thereby providing SOD heat stability at a temperature of at least about 45° C.

83. The cosmetic composition of claim 82, wherein said sugar is selected from the group consisting of maltitol and trehalose, and said polyol is mannitol.

84. The cosmetic composition of claim 82, wherein the peroxidase is a black radish peroxidase extract in an amount of peroxidase, expressed in a ratio of peroxidase units with respect to SOD units of about 10/400, and a cosmetically acceptable peroxidase cofactor at a concentration between 0.001M and 1M.

85. The cosmetic composition of claim 82, wherein the polyol is maltitol.

86. A composition with anti-free radical activity selected from the group consisting of a cosmetic composition, a pharmaceutical composition and a food composition, comprising as an active ingredient a plant superoxide dismutase (SOD) obtained by extraction from germinated plant seeds, said SOD being stabilized first by addition of a cosmetically, pharmaceutically or food acceptable peroxidase and peroxidase cofactor, and then by addition of a SOD stabilizing effective amount of maltitol, in a cosmetically, pharmaceutically or food acceptable excipient, thereby providing SOD heat stability at a temperature of at least about 45° C.

87. A cosmetic composition comprising as one of the active ingredients a plant extract comprising superoxide dismutase (SOD) obtained by extraction from germinated plant seeds, said SOD being present at a concentration ranging from 0.01 to 10% by weight with respect to the total weight of the composition, a cosmetically acceptable peroxidase, a cosmetically acceptable peroxidase cofactor, and maltitol, at a concentration ranging between 10 and 50% by weight of SOD component selected from the group consisting of SOD and of SOD/peroxidase/peroxidase cofactor, in a cosmetically acceptable excipient, thereby providing SOD heat stability at a temperature of at least about 45° C.

* * * * *